United States Patent [19]

Furihata

[11] 4,224,929

[45] Sep. 30, 1980

[54] ENDOSCOPE WITH EXPANSIBLE CUFF MEMBER AND OPERATION SECTION

[75] Inventor: Hiroyuki Furihata, Tokyo, Japan

[73] Assignee: Olympus Optical Co., Ltd., Tokyo, Japan

[21] Appl. No.: 957,567

[22] Filed: Nov. 3, 1978

[30] Foreign Application Priority Data

Nov. 8, 1977 [JP] Japan .......................... 52-149794[U]
Nov. 8, 1977 [JP] Japan .......................... 52-149796[U]

[51] Int. Cl.³ .............................................. A61B 1/00
[52] U.S. Cl. .................................................. 128/5; 128/6
[58] Field of Search ........................................ 128/3-8,
128/325, 349 B, 349 BU, 633-634; 356/241; 350/96.26, 96.25

[56] References Cited

U.S. PATENT DOCUMENTS

| 3,154,077 | 10/1964 | Cannon | 128/349 B X |
| 3,417,745 | 12/1968 | Sheldon | 128/6 |
| 3,690,769 | 9/1972 | Mori | 350/96.26 X |
| 3,866,599 | 2/1975 | Johnson | 128/6 X |
| 3,889,686 | 6/1975 | Dutarbure | 128/349 B |
| 3,903,877 | 9/1975 | Terada | 128/6 |
| 4,040,413 | 8/1977 | Ohshiro | 128/6 |

Primary Examiner—Robert W. Michell
Assistant Examiner—Jeffrey W. Tayon

[57] ABSTRACT

An endoscope includes a distal end section, a pair of axially spaced annular cuffs mounted on the distal end section or a cuff member mounted on the distal end section having an opening formed in its intermediate portion and sealingly fitted at its edge portions on the distal end section, and a chamber formed in the distal end section and opened at the opening in the cuff member. By the expansion of the cuffs or the cuff member, a closed space is defined by the inner surface of a body cavity where an affected part exists, and the cuffs or the cuff member, and a medical instrument is accessible to the affected part through the chamber with blood or other body fluids cleared from the space during the treatment of the affected part. A communication duct extends along the digital end section such that it allows the blood or other body fluids to freely flow in the body cavity while the affected part is being treated.

10 Claims, 9 Drawing Figures

ENDOSCOPE WITH EXPANSIBLE CUFF MEMBER AND OPERATION SECTION

BACKGROUND OF THE INVENTION

This invention relates to an endoscope which is inserted into a body cavity such as a heart, a blood vessel and a tubular body cavity including bled blood or an opaque body fluid and with which an operator can treat an affected portion in the body cavity while he is observing the interior of the tubular body cavity in spite of the blood or other body fluid.

As shown in FIG. 1, a known endoscope such as a cardiofiberscope used in a tubular body cavity containing blood or other body fluid comprises a distal end section 1, an observation optical system 2 and as illumination system 3 both disposed in the section 1 and a transparent cuff 4 attached to the free end of the section 1. The cuff 4 communicates with an air channel 5 and is inflated with air supplied through the air channel 5. When inflated, the cuff 4 contacts the inner surface of a tubular body cavity, thus expelling or clearing blood or other body fluid from the space between the illumination optical system 2 and the illumination system 3 and the inner surface of the tubular body cavity. This allows an operator to observe the inner surface of the body cavity without blur due to the blood or other body fluid.

Indeed it is possible with the prior art endoscope to observe the inner surface of a tubular body cavity. But it is impossible with it to use a medical instrument such as forceps and thus to pick up tissues from the body cavity or stop bleeding in the body cavity.

SUMMARY OF THE INVENTION

An object of the present invention is to provide an endoscope the distal end section of which is inserted into a tubular body cavity and with which an operator can pick up tissues from the body cavity or stop bleeding in the body cavity, while he is observing the inner surface of the body cavity.

An endoscope according to the invention comprises a distal end section, a first transparent cuff sealingly surrounding the distal end portion of the distal end section, an observation optical system disposed in the distal end section, an illumination optical system disposed in the distal end section, a second cuff sealingly surrounding the proximal end portion of the distal end section in a relation spaced axially of the distal end section from the first cuff, and a channel for conducting fluid and for guiding a medical instrument, which channel extends through the distal end section and opens between the first and second cuffs.

Another endoscope according to the present invention is provided with one transparent cuff which surrounds substantially whole outer periphery of the distal end section with an intermediate part thereof partially left uncovered. In the endoscope a channel for conducting fluid and for guiding a medical instrument opens at that intermediate part of the distal end section which is not covered with the cuff.

In a desired position in a tubular body cavity the cuffs are inflated until they push the inner surface of the body cavity, thereby expelling or clearing blood from the space defined by the cuffs and the inner surface of the body cavity. After all the blood or other body fluid has been expelled from the space, an operator can insert a medical instrument into the body cavity through the channel and treat an affected portion of the body cavity, while he is clearly observing the affected portion owing to the absence of the blood or other body fluid in the space.

A communication duct may extend through the distal end section beyond the cuff or cuffs such that its both ends open at those distal and proximal end portions of the section where the space and the cuff or cuffs are not disposed. Thus the duct permits a blood flow in the tubular body cavity while the cuff or cuffs are being inflated.

DETAILED DESCRIPTION OF THE PREFERRED EMBODIMENTS

Figure 1:
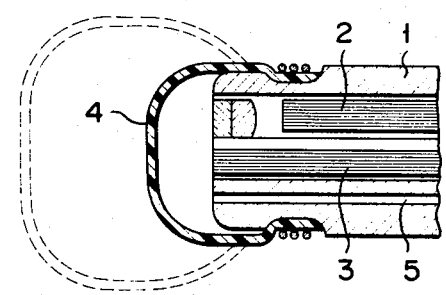
FIG. 1 is a longitudinal sectional view of the distal end section of a known endoscope having a cuff.
Figure 2:
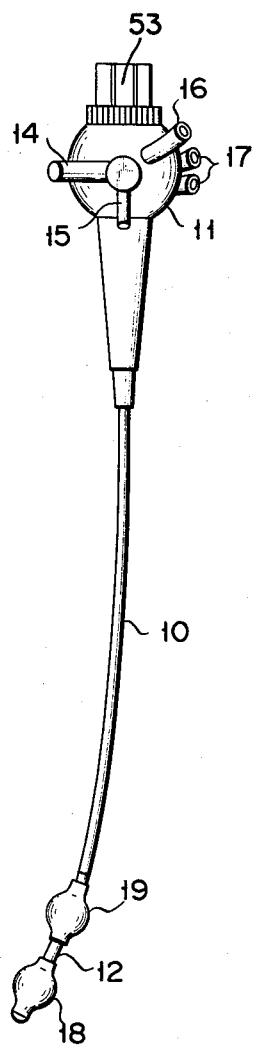
FIG. 2 is a whole view of an endoscope according to the present invention.

As shown in FIG. 2, an endoscope comprises a flexible sheath 10, a control section 11 fixed to the proximal end of the sheath 10 and a distal end section 12 fixed to the distal end of the sheath 10. The control section 11 is provided with an angle control lever 14, a direction control lever 15, an instrument inlet 16 and two fluid inlets 17. The angle control lever 14 is operated to determine the deflecting angle of the distal end section 12. The direction control lever 15 is operated to determine the direction in which a medical instrument such as a forceps is to extend from the distal end section 12. Through the inlet 16 the medical instrument is inserted into the sheath 10 and then the forward end portion thereof is extended into a body cavity. Mounted on the proximal end of the control section 11 is an ocular or an eyepiece 53 which is optically connected to the later described image guide.

Figure 3:
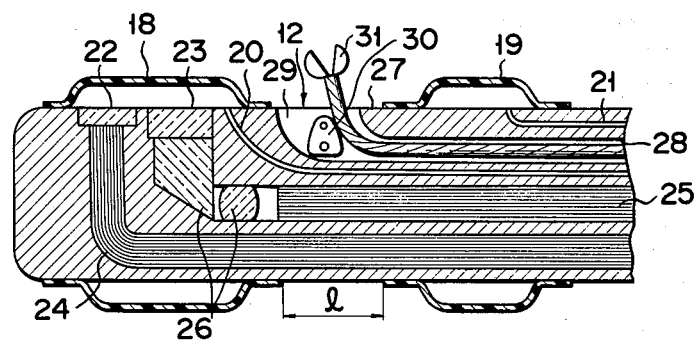
FIG. 3 is a longitudinal sectional view of the distal end section of an embodiment of the present invention.

As illustrated in FIG. 3, two transparent annular expansible cuff members 18 and 19 made of polyurethane resin or the like are sealingly provided so as to surround the distal end part and proximal end part of the distal end section 12, respectively. The cuffs 18 and 19 are spaced from each other for a distance l and can be inflated in the radial direction of the distal end section 12. Two fluid passages 20 and 21 open in the cuffs 18 and 19, respectively, and extend to the fluid inlets 17 through the distal end section 12, the flexible sheath 10 and the control section 11. The distal end part of the section 12 has an illumination window 22 and an observation window 23 side by side and are surrounded by the cuff 18. A light guide 24 extending through the sheath 10 is optically connected to the illumination window 22. An image guide 25 extending through the sheath 10 is optically connected to the observation window 23 via optical elements 26 such as a lens and a prism. In a part 27 of the distal end section 12 between the cuffs 18 and 19 there is formed a chamber 29 which communicates with a channel 28 extending through the sheath 10 and which opens at said part 27. A rocking cam 30 is mounted pivotally in the chamber 29. The cam 30 is rotated by the direction control lever 15 via a wire, and its angle of rotation determines the direction toward which an elongated medical instrument 31 such as a forceps is directed.

Figure 4:
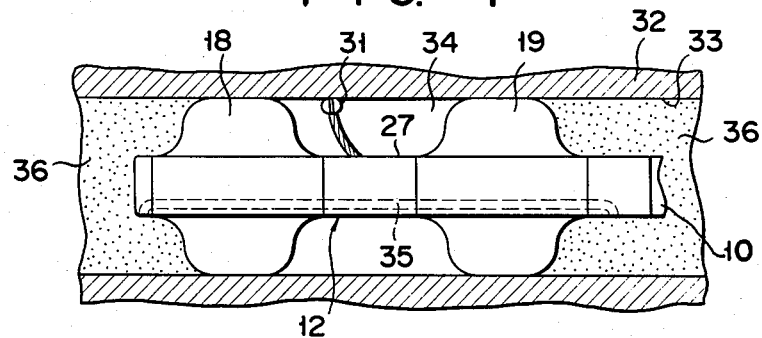
FIG. 4 is a schematic view showing the operation of the distal end section of the endoscope of FIG. 3.

With reference to FIG. 4 it will be described how the endoscope shown in FIG. 3 is operated. First, the distal end section 12 of the endoscope is inserted into a desired part of a tubular body cavity 32. A transparent fluid such as carbon dioxide gas or physiological salt solution is pumped into the cuffs 18 and 19 through the fluid passages 20 and 21, respectively, thereby inflating or expanding the cuffs 18 and 19 until they contact and push the inner surface 33 of the body cavity 32. The inflated cuffs 18 and 19, the part 27 of the distal end section 12 and the inner surface 33 of the body cavity 32 therefore define a space 34 which is sealingly separated from other space in the body cavity 32. The blood or other body fluid in the space 34 is sucked out through the channel 28. Thereafter the operator observes and examines through the observation window 23 and the cuff 18 that part of the inner surface 33 which defines the space 34. If an affected portion which is searched for is not found on said part of the inner surface 33, the fluid is sucked out from both cuffs 18 and 19 through the channel 28. Then, the distal end section 12 is moved repeatedly in the body cavity 32 and the cuffs 18 and 19 are inflated repeatedly until the affected portion is found between the cuffs 18 and 19. When the affected portion is found between the cuffs 18 and 19, an elongated medical instrument 31 such as a forceps is inserted into the channel 28 to have its distal end portion protruded into the space 34 through the chamber 29. Then the cam 30 is rotated by the direction control lever 15 so as to direct the medical instrument 31 to the affected portion. The medical instrument 31 is further fed until it reaches the affected portion. The instrument 31 is then manipulated to take tissues from the affected portion, stop the bleeding of the affected portion or make other necessary medical treatments.

In the embodiment of FIG. 3, the illumination window 22 and the observation window 23 are surrounded by the cuff 18. Instead they may be surrounded by the cuff 19.

If the endoscope is used in a body cavity such as the heart and blood vessel in which blood is always flowing, the distal end section 12 may be provided with such a duct communication 35 as illustrated in FIG. 4 in dotted lines. The duct 35 extends substantially parallel to the axis of the section 12 and its distal end opens at that outer peripheral portion of the section 12 which is nearer to the distal end of the section 12 than the distal side edge of the cuff 18, and the other end opens at that outer peripheral portion of the section which is nearer to the proximal end of the section 12 than the proximal side edge of the cuff 19. Thus, the blood can flow through the duct 35 even if both cuffs 18 and 19 are inflated and push the inner surface 33 of the body cavity 32. In other words, the operator can observe the affected portion and make a treatment without stopping the flow of blood in the body cavity 32.

Figure 5:
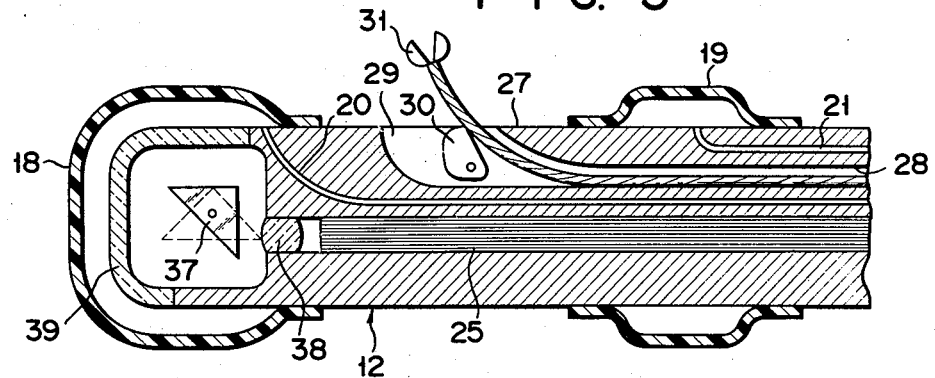
FIG. 5 is a longitudinal sectional view of the distal end section of another embodiment of the present invention.

FIG. 5 shows an endoscope of direct view type according to the invention. The distal end section 12 is provided in its distal end part with an objective lens 38 and a prism 37 positioned nearer to the distal end of a distal end section 12 than the lens 38. The prism 37 is optically connected to the distal end of an image guide 25 by the lens 38. The prism 37 is so rotated as to select a view field. The prism 37 is disposed in a cup-shaped cover 39 made of, for example, transparent glass or plastic material. Further, the distal end part of the section 12 is covered with a cuff 18. Except for these features, the endoscope is constructionally identical with the endoscope shown in FIG. 3. With this endoscope, it is possible for an operator to observe a wide range of the inner surface of the body cavity, thereby to make an easy, quick treatment on an affected portion in a tubular body.

Figure 6:
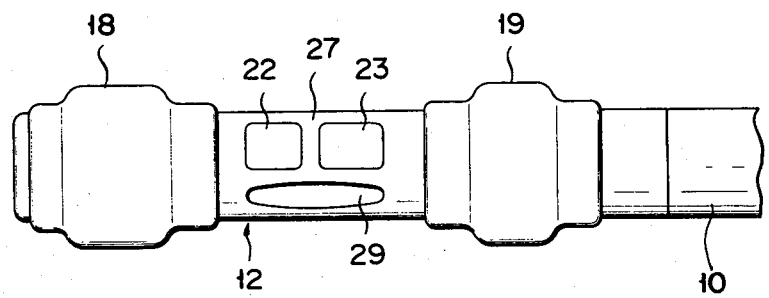
FIGS. 6 to 8 are front views of the distal end sections of further embodiments of the present invention, respectively.

In the embodiment of FIG. 6 an illumination window 22 and an observation window 23 open at an intermediate part of a distal end section 12 between a cuff 18 and a cuff 19. Except for this feature this endoscope is constructionally identical with the endoscope shown in FIG. 3. Since both the illumination window 22 and the observation window 23 are located very close to a chamber 29, the inner surface of a body cavity can be observed quite close to that end portion of a medical instrument such as forceps which protrudes from the chamber 29 into the body cavity. This makes it easier for the operator to handle the medical instrument.

Figure 7:
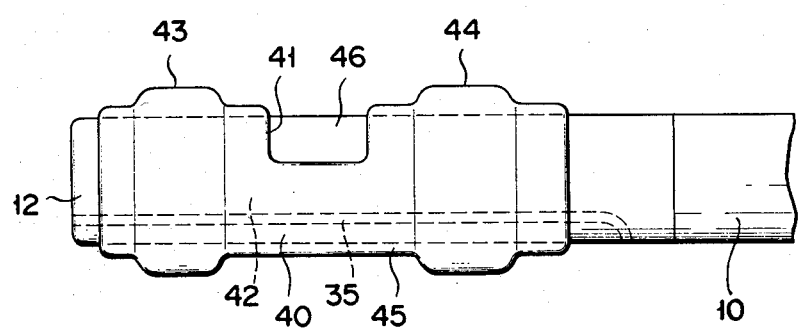

FIG. 7 shows a distal end section 12 which differs from the distal end sections 12 of FIGS. 3 to 6 in that a single expansible cuff member 45 is provided instead of two cuffs 18 and 19. The cuff member 45 is mounted on the distal end section 12. The member 45 consists of an intermediate portion 42 reduced in its diameter and two cuff portions 43 and 44 integrally formed at the respective sides of the intermediate portion 42. The intermediate portion 42 is fitted on the outer periphery of the section 12 and has an opening 41. At a portion 46 of the distal end section 12 where the opening 41 lies only a chamber 29 opens as in the embodiments of FIGS. 3 to 6; or a chamber 29, an illumination window 22 and an observation window 23 open as in the embodiment of FIG. 6. If the endoscope is used in a body cavity through which a blood flows, such a duct 35 as shown in FIG. 4, may be provided in the distal end section 12 thereby to prevent a blocking of blood flow.

Figure 8:
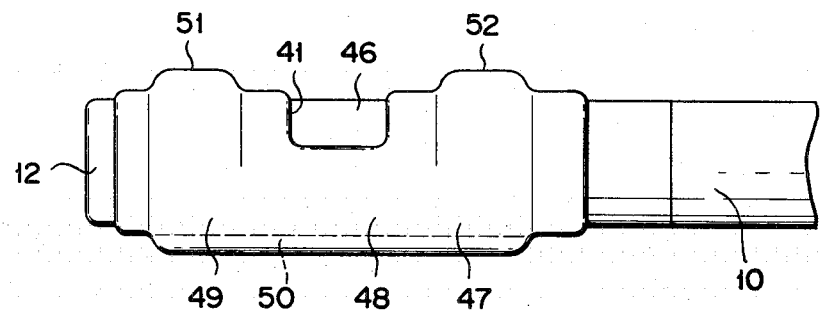
Figure 9:
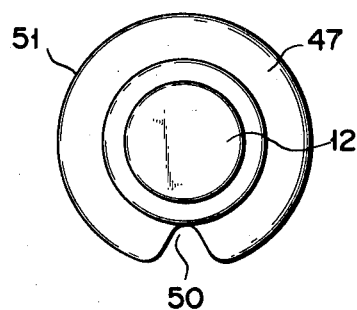
FIG. 9 shows a modified distal end section shown from that of FIG. 8.

FIG. 8 illustrates another distal end section 12. A cuff member 47 is closely fitted with the distal end section 12 only at its both end portions and at the edge portions of an opening 41 formed at its intermediate portion. The remaining portion of the cuff member 47 can be inflated and thus constitutes a balloon 49. Unlike the distal end section 12 of FIG. 7 which requires two fluid passages for the cuff portions 43 and 44, respectively, the distal end section 12 of FIG. 8 needs only one fluid passage. A duct 50 may be provided to extend, as shown in FIG. 9, through the entire length of the cuff 49 so as to avoid blocking of blood flow in a body cavity. As fluid is pumped into the cuff 49 through the fluid passage, the cuff 49 is inflated gradually until it pushes the inner surface of the body cavity, and a closed space is defined by the inner surface of the body cavity, inflated cuff portions 51 and 52 formed at both the axial sides of the opening 41 and those portions of the cuff 49 which are adjacent to the edge of the opening 41. The blood or other body fluid are sucked out of the space through the fluid passage. Since blood or other body fluid does not exist in the space while the cuff 49 is being inflated, the inner surface of the body cavity between the inflated cuff portions 51 and 52 can be observed clearly. If an affected portion which is searched for is not found on the inner surface of the body cavity, the distal end section 12 is repeatedly moved and the cuff portion 49 is repeatedly inflated until the affected portion is located between the inflated cuff portions 51 and 52.

What is claimed is:

1. An endoscope comprising:

a flexible sheath having two ends;

a control section connected to one of said two ends of the sheath;

an elongated distal end section connected to the other end of the sheath and having an outer periphery;

a single, unitary expansible cuff member mounted on the outer periphery of the distal end section and provided at an intermediate part of said cuff with an opening being defined by said cuff, said cuff member having a portion thereof defining a peripheral edge of said opening, said peripheral edge being sealingly fixed to the outer periphery of the distal end section so that said cuff member is sealingly engaged on said distal end section, said cuff member having an end portion on either end of said opening, said end portions being spaced longitudinally of said distal end section and sealingly fixed to the outer periphery of the distal end section;

an illumination window and observation window both provided in the outer periphery of said distal end section and disposed within said cuff member;

fluid passage means extending through said sheath and in said control section and said distal end section and communicating with said cuff member for conducting a fluid into said cuff member for inflation thereof, the sealing contact between said cuff and said distal end section adjacent said cuff member opening preventing fluid from escaping from said cuff member;

fluid inlet means provided on said control section and communicating with said fluid passage means for conducting fluid from a source into said fluid passage means;

illuminating light transmitting means extending through said sheath and in said distal end section and control section and having two end areas, one end area being optically connected to said illumination window;

observation light transmitting means extending in said distal end section and through said sheath and said control section having two extremities, one extremity being optically connected to said observation window;

an ocular mounted on said control section and optically connected to another extremity of said observation light transmitting means;

a chamber formed in said distal end section and opening at that portion of the outer periphery of said distal end section which is disposed in the opening of the cuff member, said chamber allowing an elongated medical instrument to be extended out of the chamber and into the space between said cuff member end portions for contacting the inner surface of a body cavity in which said distal end section is located;

a channel extending through said sheath and in said distal end section and said control section and having first and second ends, said first end communicating with said chamber, said channel being adapted to guide a medical instrument to said chamber; and an instrument inlet mounted on said control section and communicating with said channel second end.

2. The endoscope according to claim 1, further including a communication duct which extends axially in said distal end section and has inlet and exit ends opening at those portions of the outer periphery of said distal end section which are disposed in said cuff member end portions to define a bypass for said cuff member.

3. The endoscope according to claim 1, wherein said cuff member is expansible radially of said distal end section as fluid is introduced into said cuff member.

4. The endoscope according to claim 3, wherein a communication duct extends axially in the distal end section and has first and second end areas opening at those portions of the outer periphery of the distal end section which are disposed beyond said cuff member to define a bypass by said cuff member.

5. The endoscope according to claim 1, wherein said cuff member except for said opening and said two end sections of the cuff member is expansible radially of said distal end section as fluid is conducted into said cuff member through said fluid passage means.

6. The endoscope according to claim 5, wherein said cuff member has a channel defining section which forms a communication channel extending along the cuff member for conducting fluid by said cuff member.

7. The endoscope according to claim 1 further including means connected to said chamber for removing material via said channel from the space defined by said cuff member ends and the internal surface of the body cavity in which said distal end is located.

8. The endoscope according to claim 1 further including instrument orienting means connected to said distal end adjacent said chamber for orienting an instrument extending out of said chamber.

9. The endoscope according to claim 8 further including an instrument control member connected to said instrument orienting means and mounted on said control section.

10. The endoscope according to claim 1 wherein the medical instrument includes forceps.

* * * * *